(12) United States Patent  
Ishihara

(10) Patent No.: US 8,049,184 B2  
(45) Date of Patent: Nov. 1, 2011

(54) FLUOROSCOPIC DEVICE AND FLUOROSCOPIC METHOD

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 189 days.

(21) Appl. No.: 12/522,601

(22) PCT Filed: Jan. 17, 2008

(86) PCT No.: PCT/JP2008/050489
§ 371 (c)(1),
(2), (4) Date: Jul. 9, 2009

(87) PCT Pub. No.: WO2008/088002
PCT Pub. Date: Jul. 24, 2008

(65) Prior Publication Data
US 2010/0059690 A1    Mar. 11, 2010

(30) Foreign Application Priority Data

Jan. 18, 2007   (JP) .................................. 2007-009284

(51) Int. Cl.
*G01N 21/64* (2006.01)
(52) U.S. Cl. ................. 250/459.1; 600/426; 600/160
(58) Field of Classification Search .................. 600/426, 600/160; 250/459.1
See application file for complete search history.

(56) References Cited

U.S. PATENT DOCUMENTS

| 5,590,660 A | 1/1997 | MacAulay et al. |
| 2005/0027166 A1* | 2/2005 | Matsumoto et al. .......... 600/162 |
| 2005/0143652 A1* | 6/2005 | Sato .............................. 600/431 |
| 2005/0153356 A1* | 7/2005 | Okawa et al. ..................... 435/6 |

FOREIGN PATENT DOCUMENTS

| JP | HEI 8-224208 | 9/1996 |
| JP | 10-500588 | 1/1998 |
| JP | 2003-517025 | 5/2003 |
| JP | 2006-175052 | 7/2006 |
| WO | WO 01/43781 A1 | 6/2001 |

* cited by examiner

*Primary Examiner* — David Porta
*Assistant Examiner* — Hugh Maupin
(74) *Attorney, Agent, or Firm* — Scully, Scott, Murphy & Presser, P.C.

(57) ABSTRACT

A lesion can be made distinctive in an acquired fluorescence image so as to allow for accurate diagnosis. There is provided a fluoroscopic device (1) including a light source unit (2) that emits illumination light, which is in a wavelength range to be absorbed by a blood vessel, and excitation light, which generates agent fluorescence by exciting a fluorochrome accumulated specifically in a lesion, to an examination site (S); an image acquisition unit (15, 16) that acquires an image by irradiating the same examination site (S) with the illumination light and the excitation light and photographing the respective reflected light and fluorescence obtained; and an image processing unit (4) that acquires a reference image by smoothing the luminance of the reflected-light image acquired by the image acquisition unit (15, 16) and corrects the fluorescence image on the basis of the acquired reference image.

4 Claims, 5 Drawing Sheets

FLUOROSCOPIC DEVICE AND FLUOROSCOPIC METHOD

TECHNICAL FIELD

The present invention relates to fluoroscopic devices and fluoroscopic methods.

BACKGROUND ART

Known endoscope systems of the related art emit excitation light, which generates agent fluorescence by exciting a fluorochrome accumulated specifically in a lesion, such as cancer cells, to an examination site, which is given the fluorochrome. The endoscope system photographs the generated agent fluorescence so as to acquire a fluorescence image having high luminance in the lesion (for example, see Patent Document 1).

Patent Document 1: Japanese Unexamined Patent Application, Publication No. Hei 8-224208

DISCLOSURE OF INVENTION

Biological tissue at the examination site naturally contains autofluorescent material, and the emission of the excitation light causes the autofluorescent material to be excited in addition to the fluorochrome. The lesion tends to become obscured in the acquired fluorescence image.

The present invention provides a fluoroscopic device and a fluoroscopic method that can make a lesion distinctive in an acquired fluorescence image so as to allow for accurate diagnosis.

A first aspect of the present invention provides a fluoroscopic device including a light source unit that emits illumination light, which is in a wavelength range to be absorbed by a blood vessel, and excitation light, which generates agent fluorescence by exciting a fluorochrome accumulated specifically in a lesion, to an examination site; an image acquisition unit that acquires an image of reflected light and an image of the fluorescence by photography, the reflected light and the fluorescence being obtained as a result of respectively emitting the illumination light and the excitation light to the same examination site; and an image processing unit that acquires a reference image by smoothing the luminance of the reflected-light image acquired by the image acquisition unit and corrects the fluorescence image on the basis of the acquired reference image.

According to the first aspect, the light source unit is actuated so as to emit illumination light and excitation light to the same examination site, and the image acquisition unit is actuated so as to acquire a reflected-light image corresponding to the illumination light and a fluorescence image corresponding to the excitation light. Because the illumination light has a wavelength range to be absorbed by blood vessels (including the blood flowing through the blood vessels), the illumination light, when emitted to the examination site, is absorbed by the blood vessels existing in the examination site. In consequence, the reflected-light image has lower luminance in the section with the blood vessels.

In this case, since a large number of blood vessels develop in a lesion, such as cancer tissue, the reflected-light image has a large number of dark areas corresponding to the blood vessels. On the other hand, since normal tissue has a smaller number of blood vessels as compared with a lesion, the reflected-light image has a smaller number of dark areas corresponding to the blood vessels.

Accordingly, by actuating the image processing unit, the luminance of the reflected-light image is smoothed so that information about the shape of the blood vessels is removed, whereby the acquired reference image has gradations such that the vicinity of the lesion is shown darker and the vicinity of the normal section is shown brighter. By using the reference image acquired in the image processing unit in this manner, the section corresponding to the lesion in the fluorescence image can be made brighter and distinctive, thereby allowing for accurate diagnosis.

In the first aspect, the image processing unit may include a low-pass filter that smoothes the luminance of the reflected-light image acquired by the image acquisition unit.

By allowing the reflected-light image information to pass through the low-pass filter, variations in luminance values, which vary depending on individual pixels, can be readily smoothed, whereby a reference image in which the luminance values vary in smooth gradation can be acquired. Consequently, it is possible to readily acquire a reference image having removed therefrom the information about the shape of the blood vessels included in the reflected-light image and showing the vicinity of the lesion as a darker region and showing the vicinity of the normal section as a brighter region.

Furthermore, in the first aspect, there may be provided a fluorescence-image corrector that performs correction by dividing a luminance value of the fluorescence image, acquired by the image acquisition unit, by a luminance value of the reference image, acquired by smoothing.

Accordingly, by actuating the fluorescence-image corrector, the luminance value of the fluorescence image is divided by the luminance value of the reference image, whereby the luminance value of the lesion, which has a high luminance value due to the agent fluorescence, is increased as a result of being divided by the luminance value of the reference image having a relatively lower luminance value. On the other hand, although there is no agent fluorescence in the normal section, even if the normal section has a high luminance value due to autofluorescence, the luminance value of the normal section is reduced by being divided by the luminance value of the reference image, which has a relatively higher luminance value. In consequence, a corrected image with a distinctive lesion can be readily acquired, thereby improving the diagnostic capability.

A second aspect of the present invention provides a fluoroscopic method including a step for emitting illumination light, which is in a wavelength range to be absorbed by a blood vessel, and excitation light, which generates agent fluorescence by exciting a fluorochrome accumulated specifically in a lesion, to a single examination site; a step for acquiring an image of reflected light and an image of the fluorescence by photography, the reflected light and the fluorescence being obtained as a result of respectively emitting the illumination light and the excitation light; and a step for acquiring a reference image by smoothing the luminance of the acquired reflected-light image, and correcting the fluorescence image on the basis of the acquired reference image.

According to the present invention, a lesion can be made distinctive in an acquired fluorescence image so as to advantageously allow for accurate diagnosis.

EXPLANATION OF REFERENCE SIGNS

Figure 1:
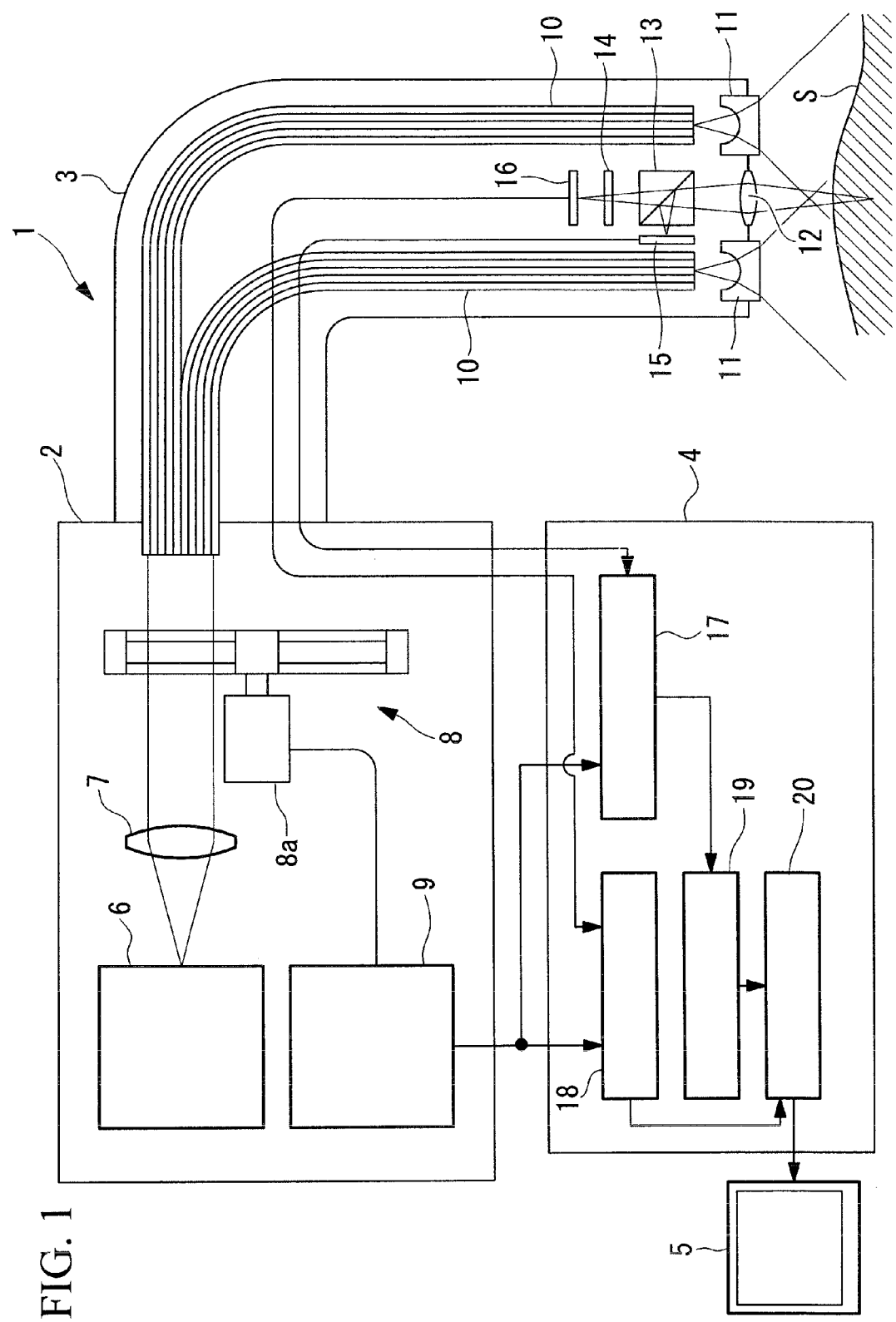
FIG. 1 schematically illustrates a fluoroscopic device according to an embodiment of the present invention.

A, B, C: filters
$G_1$: reflected-light image
$G_2$: reference image
$G_3$, $G_3'$: agent-fluorescence image
S: examination site
T: blood vessel
X: lesion (tumor section)
1: fluoroscopic device
2: light source unit
4: image processing unit
15: reflected-light image acquisition element (image acquisition unit)
16: fluorescence image acquisition element (image acquisition unit)
19: reference-image generator
20: fluorescence-image corrector

BEST MODE FOR CARRYING OUT THE INVENTION

A fluoroscopic device 1 according to an embodiment of the present invention will be described below with reference to FIGS. 1 to 7.

The fluoroscopic device 1 according to this embodiment includes a light source unit 2, an insertion section 3, an image processing unit 4, and a monitor 5, as shown in FIG. 1.

The light source unit 2 includes a white light source 6 that generates white light, a collimator lens 7 that substantially collimates the white light from the white light source 6, a rotating filter 8 that extracts light of a predetermined wavelength range from the white light, and a filter controller 9 that controls the rotating filter 8.

Figure 2:
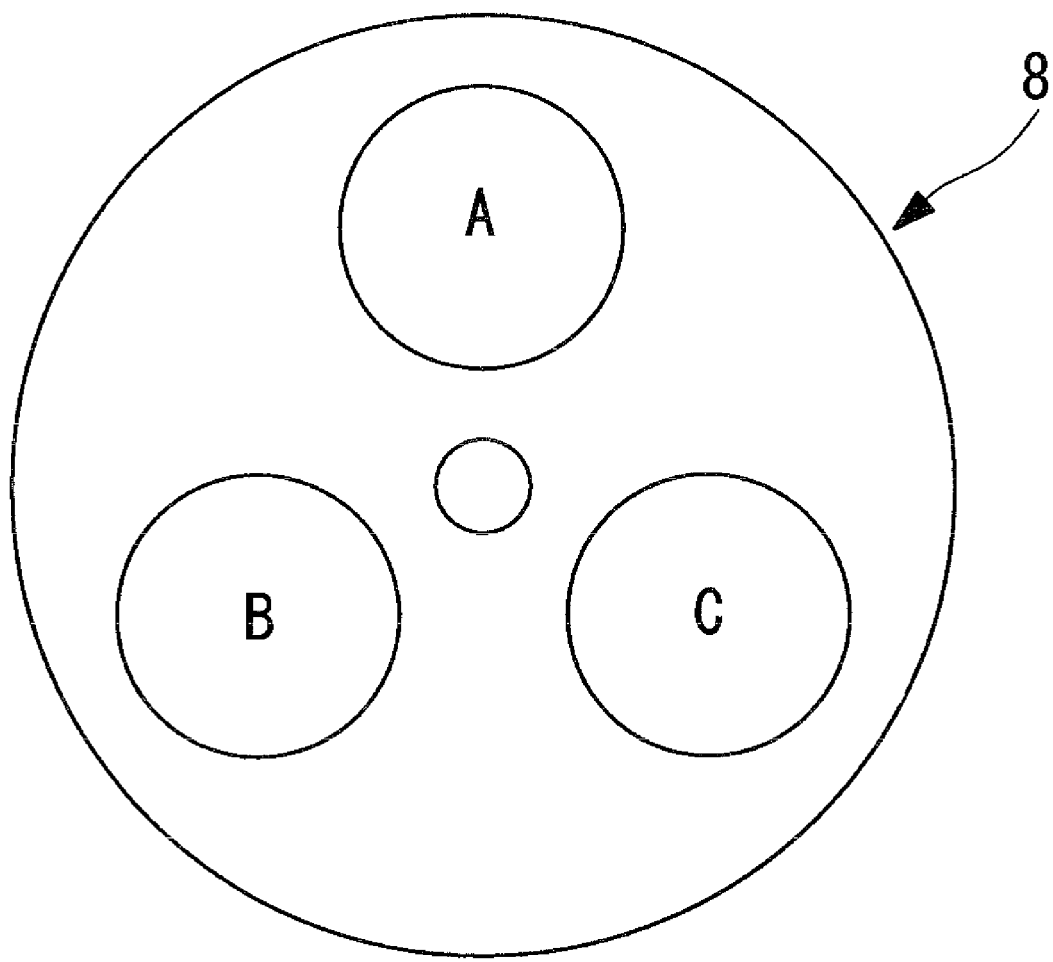
FIG. 2 illustrates an example of a rotating filter included in the fluoroscopic device shown in FIG. 1.
Figure 3:
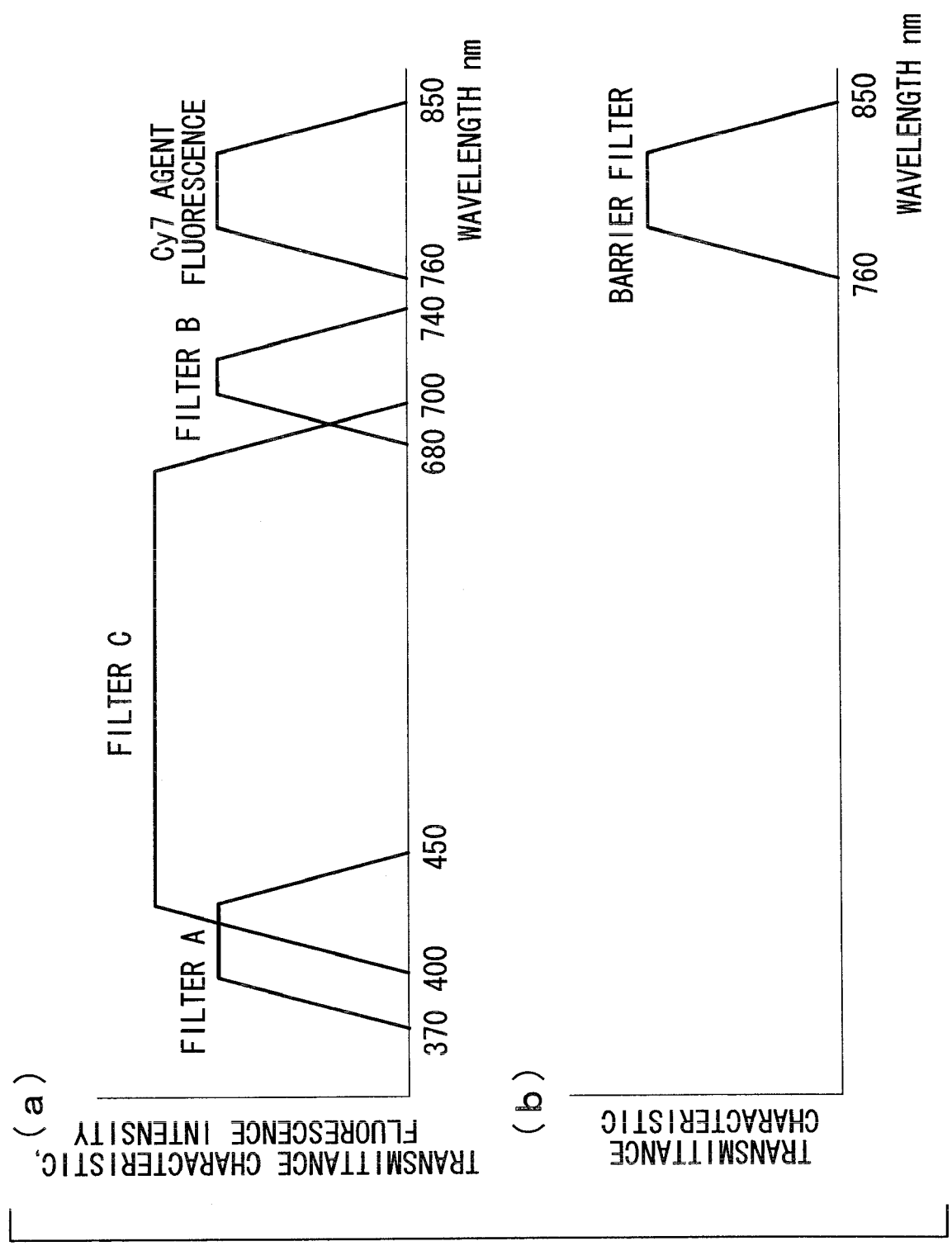
FIG. 3 includes graphs showing a transmittance characteristic of each filter of the rotating filter shown in FIG. 2 and a fluorescence wavelength characteristic.

As shown in FIG. 2, the rotating filter 8 has three different filters A, B, and C. As shown in FIG. 3, these filters A, B, and C have transmittance characteristics such that the filter A transmits light in a wavelength range between 370 nm and 450 nm inclusive, the filter B transmits light in a wavelength range between 680 nm and 740 nm inclusive, and the filter C transmits light in a wavelength range between 400 nm and 700 nm inclusive.

The light in the wavelength range between 370 nm and 450 nm inclusive extracted by the filter A has a characteristic such that when it is emitted to an examination site S, which includes biological tissue, the light is absorbed by blood vessels existing in the biological tissue of the examination site S.

The light in the wavelength range between 680 nm and 740 nm inclusive extracted by the filter B has a characteristic such that it excites a fluorescent agent, such as Cy7 (manufactured by Amersham Inc.), which accumulates specifically in a lesion, such as a tumor, so as to produce fluorescence in a wavelength range between 760 nm and 850 nm inclusive.

By rotationally driving a motor 8a in response to a command signal from the filter controller 9, the rotating filter 8 sequentially switches between the filters A, B, and C so that light of different wavelength ranges can be emitted to the same examination site S.

The filter controller 9 is configured to output information about the filter A, B, or C disposed in the optical path as a trigger signal to the image processing unit 4 to be described later.

The insertion section 3 is, for example, formed to be narrow and bendable so that it can be inserted into a body cavity. The insertion section 3 includes light guide fibers 10 for guiding light emitted from the light source unit 2, a lens 11 that expands the light guided to the tip by the light guide fibers 10 and outputs it to the examination site S, an objective lens 12 that collects fluorescence or reflected light returning from the examination site S, a dichroic mirror 13 that causes the collected fluorescence and reflected light to be separated from each other towards different optical paths, a barrier filter 14 that blocks excitation light included in the separated fluorescence, a reflected-light image acquisition element 15 that detects the separated reflected light, and a fluorescence image acquisition element 16 that detects the fluorescence transmitted through the barrier filter 14.

As shown in FIG. 3, of the light separated from the reflected light by the dichroic mirror 13, the barrier filter 14 has transmittance characteristics such that it transmits only the fluorescence in a wavelength range between 760 nm and 850 nm inclusive, which corresponds to agent fluorescence, and blocks the remaining light.

The reflected-light image acquisition element 15 and the fluorescence image acquisition element 16 are each formed of a solid-state image-acquisition device, such as a CCD.

The image processing unit 4 includes a reflected-light image generator 17 that generates a reflected-light image on the basis of reflected-light image information sent from the reflected-light image acquisition element 15 and the trigger signal sent from the filter controller 9, a fluorescence-image generator 18 that generates an agent-fluorescence image on the basis of fluorescence-image information sent from the fluorescence image acquisition element 16 and the trigger signal sent from the filter controller 9, a reference-image generator 19 that generates a reference image by processing the reflected-light image, and a fluorescence-image corrector 20 that corrects the agent-fluorescence image on the basis of the generated reference image.

In response to the trigger signal sent from the filter controller 9, the reflected-light image generator 17 detects a period in which the filter A is disposed in the optical path and stores the image information sent from the reflected-light image acquisition element 15 within that period as a reflected-light image.

In response to the trigger signal sent from the filter controller 9, the fluorescence-image generator 18 detects a period in which the filter B is disposed in the optical path and stores the image information sent from the fluorescence image acquisition element 16 within that period as an agent-fluorescence image.

The reference-image generator 19 is formed of a low-pass filter that smoothes the luminance of the reflected-light image acquired by the reflected-light image acquisition element 15.

In detail, the filter A disposed in the optical path when a reflected-light image is to be generated extracts light, from the white light, in a wavelength range that is to be absorbed by blood vessels. Therefore, when light in that wavelength range is emitted, the light is absorbed by a region corresponding to the blood vessels in the examination site S, thereby reducing the amount of reflected light.

Figure 4:
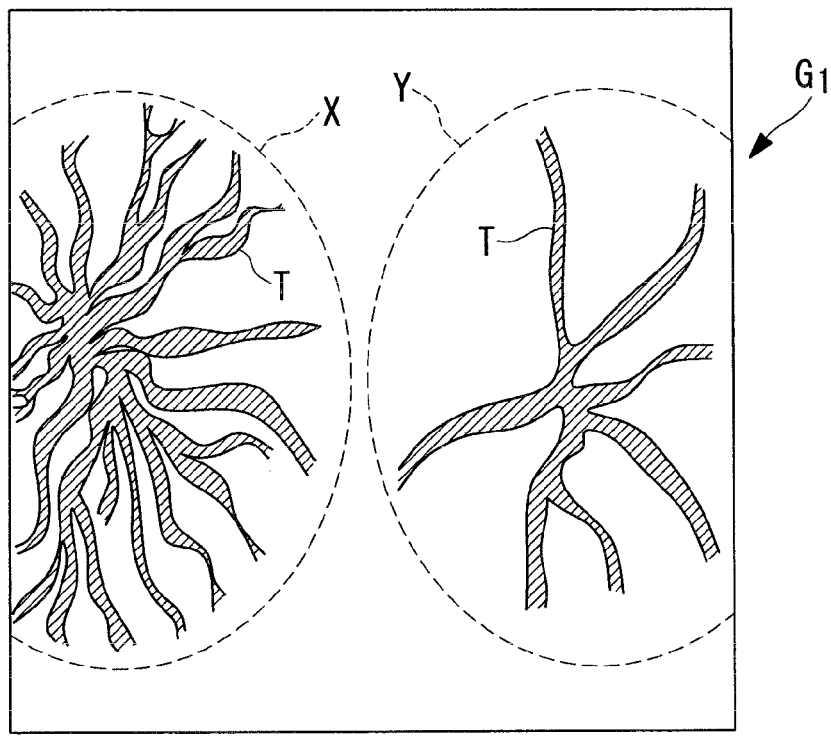
FIG. 4 illustrates an example of a reflected-light image acquired by the fluoroscopic device shown in FIG. 1.

Specifically, as shown in FIG. 4, an acquired reflected-light image $G_1$ is an image in which regions corresponding to blood vessels T are darker than the other regions. Although light absorption also occurs in the other regions since there are capillary vessels substantially uniformly over the entire surface thereof, the amount of blood existing therein is smaller, and therefore, light is not absorbed as much as it is by the thick blood vessels. Thus, the other regions are brighter than the regions corresponding to the thick blood vessels.

Figure 5:
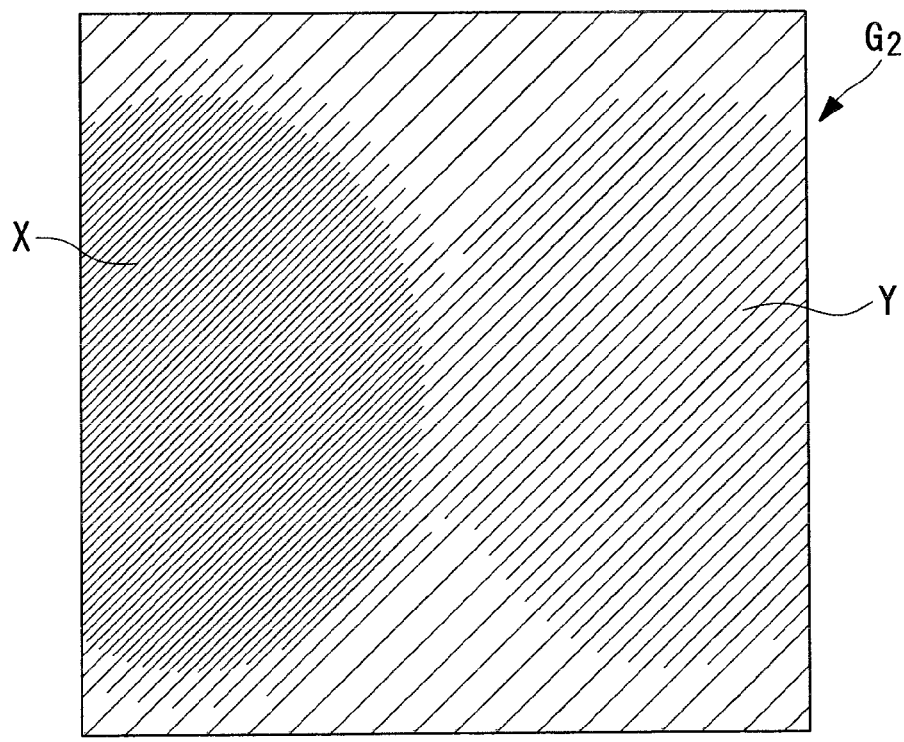
FIG. 5 illustrates an example of a reference image acquired by smoothing the reflected-light image shown in FIG. 4.

By supplying the reflected-light image $G_1$ to the reference-image generator 19 formed of a low-pass filter, fine luminance variations are removed from the reflected-light image $G_1$, whereby a reference image $G_2$ is acquired, as shown in FIG. 5, which has gradations such that a region with a larger number of thick blood vessels is shown as a darker region, whereas a region with a smaller number of thick blood vessels is shown as a brighter region.

For example, in the example shown in FIG. 5, the generated reference image has a darker region (i.e., the left region in the drawing) corresponding to a tumor section X, and the vicinity thereof, having a larger number of blood vessels T and a brighter region (i.e., the right region in the drawing) corresponding to a normal section Y, and the vicinity thereof, having a smaller number of blood vessels T.

Finally, the fluorescence-image corrector 20 divides a luminance value of an agent-fluorescence image $G_3$, generated by the fluorescence-image generator 18, by a luminance value of the reference image $G_2$, generated by the fluorescence-image corrector 20, so as to acquire a corrected agent-fluorescence image $G_3'$.

Figure 6:
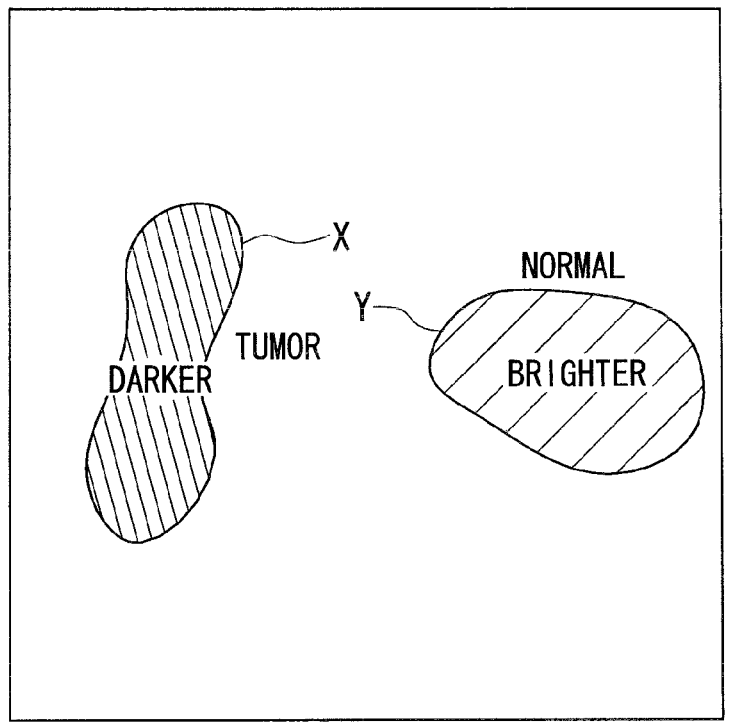
FIG. 6 illustrates an example of an agent-fluorescence image acquired by the fluoroscopic device shown in FIG. 1.

For example, FIG. 6 shows an example where the acquired agent-fluorescence image $G_3$ includes the tumor section X in which the fluorescent agent specifically accumulated therein exhibits high luminance and the normal section Y which exhibits higher luminance than the tumor section X due to being disposed closer to the lens 11.

Figure 7:
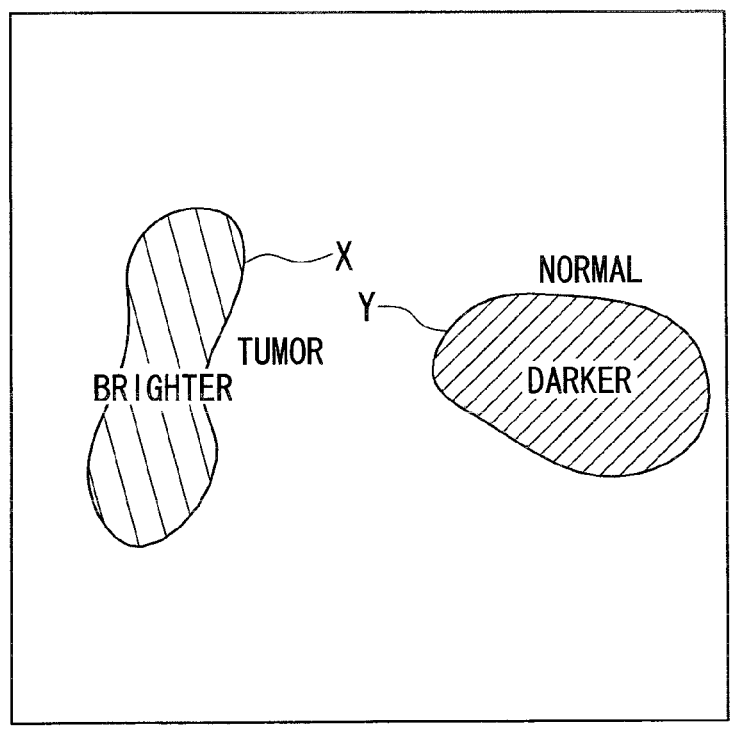
FIG. 7 illustrates an example of an image acquired by correcting the agent-fluorescence image, acquired by the fluoroscopic device shown in FIG. 1, on the basis of the reference image.

In this case, if only the agent-fluorescence image $G_3$ is observed, the normal section Y and the tumor section X, which exhibit high luminance, are not clearly distinguishable from each other, possibly leading to a diagnosis error. In light of this, the fluorescence-image corrector 20 divides the luminance value of the agent-fluorescence image $G_3$ in FIG. 6 by the luminance value of the reference image $G_2$ in FIG. 5 so as to increase the luminance of the region corresponding to the tumor section X and the vicinity thereof and reduce the luminance of the region corresponding to the normal section Y and the vicinity thereof, whereby an agent-fluorescence image $G_3'$ with a distinctive tumor section X can be acquired, as shown in FIG. 7.

A fluoroscopic method using the fluoroscopic device 1 according to this embodiment having the above configuration will be described below.

In the fluoroscopic method according to this embodiment, the insertion section 3 is inserted into a body cavity so that the tip thereof is made to face the examination site S. In this state, the light source unit 2 is actuated so that light in the wavelength range between 370 nm and 450 nm inclusive, light in the wavelength range between 680 nm and 740 nm inclusive, and white light in the wavelength range between 400 nm and 700 nm inclusive are emitted in a switching manner to the same examination site S. In this case, the white light in the wavelength range between 400 nm and 700 nm inclusive is used for checking the examination site S with visible light during manipulation of the insertion section 3, but the description thereof will be omitted here.

As a result of the emission of light in the wavelength range between 370 nm and 450 nm inclusive, reflected-light image $G_1$ information is acquired by the reflected-light image acquisition element 15. Furthermore, as a result of the emission of light in the wavelength range between 680 nm and 740 nm inclusive, agent-fluorescence image $G_3$ information is acquired by the fluorescence image acquisition element 16.

In the fluoroscopic method according to this embodiment, the correction process is performed by dividing a luminance value of the agent-fluorescence image $G_3$ by a luminance value of the reference image $G_2$, which is acquired by smoothing the acquired reflected-light image $G_1$.

Since the light in the wavelength range between 370 nm and 450 nm inclusive is absorbed by the blood vessels T, the reflected-light image $G_1$ information acquired in that state is an image having a lower luminance value in the region with the thick blood vessels T. Therefore, it is possible to readily acquire a reference image $G_2$ in which the luminance varies smoothly and in which the region with a larger number of blood vessels T, like the tumor section X, is shown as a darker region and the region with a smaller number of blood vessels T, like the normal section Y, is shown as a brighter region.

By correcting the agent-fluorescence image $G_3$ using the reference image $G_2$ acquired in this manner, the tumor section X can be made distinctive, thereby advantageously allowing for accurate diagnosis.

Although the rotating filter 8 in this embodiment is described as having three filters A, B, and C, the filter C for emitting white light is not necessarily a required component, as mentioned above.

Furthermore, although light in the wavelength range between 370 nm and 450 nm inclusive is emitted as a wavelength range to be absorbed by the blood vessels T in this embodiment, light in a wavelength range between 500 nm and 600 nm inclusive may alternatively be emitted. Since light in this wavelength range between 500 nm and 600 nm inclusive is absorbed by blood vessels T located deeper in biological tissue, a tumor section X having blood vessels at deeper locations can be made more distinctive.

Light in a narrower wavelength range, including a wavelength of 410 nm or 540 nm, may be used as the light in the wavelength range between 370 and 450 inclusive or between 500 nm and 600 nm inclusive.

Although the rotating filter 8 having the multiple filters A, B, and C is described as an example of a wavelength selector, the present invention is not limited to this example and may employ an alternative tunable spectroscopic element.

Furthermore, the insertion section 3 may be of a rigid type.

The invention claimed is:

1. A fluoroscopic device comprising:
    a light source unit that emits illumination light, which is in a wavelength range between 370 nm and 450 nm inclusive or between 500 nm and 600 nm inclusive to be absorbed by a blood vessel, and excitation light, which generates agent fluorescence by exciting a fluorochrome accumulated specifically in a lesion, to an examination site;
    an image acquisition unit that acquires an image by irradiating the same examination site with the illumination light and the excitation light and photographing the respective reflected light and fluorescence obtained; and an image processing unit that acquires a reference image by smoothing the luminance of the reflected-light image acquired by the image acquisition unit and corrects the fluorescence image on the basis of the acquired reference image.

2. The fluoroscopic device according to claim 1, wherein the image processing unit includes a low-pass filter that smoothes the luminance of the reflected-light image acquired by the image acquisition unit.

3. The fluoroscopic device according to claim 1, wherein the image processing unit includes a fluorescence-image corrector that performs correction by dividing a luminance value of the fluorescence image, acquired by the image acquisition unit, by a luminance value of the reference image, acquired by smoothing.

4. A fluoroscopic method comprising:
a step for emitting illumination light, which is in a wavelength range between 370 nm and 450 nm inclusive or between 500 nm and 600 nm inclusive to be absorbed by a blood vessel, and excitation light, which generates agent fluorescence by exciting a fluorochrome accumulated specifically in a lesion, to a single examination site;
a step for acquiring an image by radiating the illumination light and the excitation light and photographing the respective reflected light and fluorescence obtained; and
a step for acquiring a reference image by smoothing the luminance of the acquired reflected-light image, and correcting the fluorescence image on the basis of the acquired reference image.

* * * * *